United States Patent [19]

Truitt et al.

[11] Patent Number: 4,749,710
[45] Date of Patent: Jun. 7, 1988

[54] IMMUNOSUPPRESSIVE AGENTS

[75] Inventors: Gary A. Truitt, Bloomfield; William R. Benjamin, Cedar Grove; Bruce H. Devens, Glen Rock; Maurice K. Gately, Montville, all of N.J.

[73] Assignee: Hoffmann-La Roche Inc., Nutley, N.J.

[21] Appl. No.: 729,326

[22] Filed: May 1, 1985

[51] Int. Cl.$^4$ ............................................. A61K 31/59
[52] U.S. Cl. .................................................. 514/167
[58] Field of Search ...................... 514/167; 260/397.2

[56] References Cited

U.S. PATENT DOCUMENTS

| | | | |
|---|---|---|---|
| 3,907,843 | 9/1975 | De Luca et al. | 260/397.2 |
| 4,224,230 | 9/1980 | De Luca et al. | 260/397.2 |
| 4,226,787 | 10/1980 | De Luca et al. | 260/397.2 |
| 4,307,231 | 12/1981 | De Luca et al. | 260/397.2 |
| 4,336,193 | 6/1982 | De Luca et al. | 260/397.2 |
| 4,340,604 | 7/1982 | Aoki et al. | 514/167 |
| 4,341,774 | 7/1982 | Aoki et al. | 514/167 |
| 4,397,847 | 8/1983 | Boris et al. | 260/397.2 |
| 4,411,833 | 10/1983 | De Luca et al. | 260/397.2 |
| 4,508,651 | 4/1985 | Baggiolini et al. | 260/397.2 |

OTHER PUBLICATIONS

Merck Index, (1978), p. 9679.
Bhalla et al., "1,25 Dihydroxyvitamin $D_3$ Inhibits Interluekin 2 . . . ", (Abstract).
Manolagas et al., "1,25 Dihydroxyvitamin $D_3$ (Calcitriol) . . . ", (Abstract).
Bhalla et al., Jour. of Clinical Endocrinology and Metabolism, vol. 57, No. 6, pp. 1308–1310, (1982).
Walter et al., Metabolism, vol. 33, No. 3, (Mar.), pp. 240–243, (1984).
Manolagas et al., Science, vol. 224, pp. 1438–1439, (1984).
Rigby et al., J. Clin. Invst., vol. 74, pp. 1451–1455, (1984).
DeLuca et al., Proc. Nat'l Acad. Sci., vol. 81, pp. 7112–7116, (1984).
Manolagas et al., Sci., vol. 221, pp. 1181–1183, (1983).
Bhalla et al., Jour. of Immunology, vol. 133, No. 4, pp. 1748–1754, (1984).

Primary Examiner—Leonard Schenkman
Assistant Examiner—Joseph A. Lipovsky
Attorney, Agent, or Firm—Jon S. Saxe; Bernard S. Leon; Matthew Boxer

[57] ABSTRACT

The invention relates to pharmaceutical compositions comprising at least one Vitamin D derivative and a method of using the pharmaceutical compositions in suppressing immune responses.

4 Claims, No Drawings

IMMUNOSUPPRESSIVE AGENTS

BRIEF SUMMARY OF THE INVENTION

The invention relates to pharmaceutical compositions comprising at least one Vitamin D derivative and methods of using the pharmaceutical compositions in suppressing immune responses.

DETAILED DESCRIPTION OF THE INVENTION

In accordance with the invention, pharmaceutical compositions comprising at least one Vitamin D derivative are utilized in modulating immune responses, or more specifically, for example, in suppressing immune responses.

The Vitamin D derivatives which are employed include ergocalciferols; fluorinated cholecalciferols; 5,6-trans-cholecalciferols; nonfluorinated 26,23-lactone cholecalciferols; 22,23-dehydro-cholecalciferols and tachysterols.

The Vitamin D derivatives which are employed in the invention are known or can be prepared, for instance, as described below in the examples. More particularly, the Vitamin D derivatives may be 1α-hydroxylated and optionally may be substituted by one or more fluorine and/or hydroxy groups.

Exemplary of the Vitamin D derivatives are the following:

1α,25-Dihydroxy-24R-fluorocholecalciferol;
1α,25-Dihydroxy-24,24-difluorocholecalciferol;
1α,24R-Dihydroxy-25-fluorocholecalciferol;
26,26,26,27,27,27-hexafluoro-1α,25-dihydroxycholecalciferol;
26,26,26,27,27,27-hexafluoro-1α,25-dihydroxy-$\Delta^{22}$-cholecalciferol;
1α,23S,25-Trihydroxycholecalciferol;
1α,25S,26-Trihydroxy-$\Delta^{22}$-cholecalciferol;
25-Hydroxyergocalciferol;
1α,25-Dihydroxycholecalciferol-26,23-lactone;
1α,25-Dihydroxyergocalciferol;
1α,25S,26-Trihydroxyergocalciferol;
1α,25R,26-Trihydroxyergocalciferol;
1α-Fluoro-25-hydroxycholecalciferol;
1α-Fluoro-24R,25-dihydroxycholecalciferol;
25-Hydroxy-5,6-trans-cholecalciferol;
1α,25-Dihydroxy-5,6-trans-cholecalciferol;
25-Hydroxytachysterol;
1α,25-Dihydroxytachysterol; and the like.

In the chemical names herein, the symbol $\Delta$ indicates a double bond beginning at the carbon designated just to the right of the symbol and ending at the next higher carbon. Thus $\Delta^{22}$ means a double bond between carbon-22 and carbon-23.

From known or readily prepared starting materials, the preparation of the following Vitamin D derivatives, is given in the Examples below, namely:

1α,25(S),26-trihydroxycholecalciferol;
1α,25(S),26-trihydroxy-$\Delta^{22}$-cholecalciferol;
1α,25(S),26-trihydroxyergocalciferol; and
$\Delta^{22}$-26,26,26,27,27,27-hexafluoro-1α,25-dihydroxycholecalciferol.

The following Vitamin D derivatives can be prepared in a manner analogous to the Examples, by using the appropriate starting material:

1α,25(R),26-trihydroxycholecalciferol;
1α,25(R),26-trihydroxy-$\Delta^{22}$-cholecalciferol; and
1α,25(R),26-trihydroxyergocalciferol.

The compounds of the invention which are lactones form salts upon reaction with strong bases such as lithium hydroxide, cesium hydroxide, potassium hydroxide, and sodium hydroxide.

The compounds of the invention, including the salts of those compounds which form salts with pharmaceutically acceptable bases, possess immunomodulatory activity, and therefore are useful as immunomodulatory, or more specifically, immunosuppressive agents.

The compositions of the invention have immunosuppressive activity and, therefore, are useful as immunosuppressive agents. The compositions of the invention are useful in the treatment of conditions caused by abnormal rise in immunological function. More particularly, the compositions of the invention are useful in the suppression of the immune response in recipients of organ transplants including but not limited to heart, heart-lung, liver, kidney, pancreas and pancreatic islet cells, and skin. Further, the compositions of the invention are also useful for therapeutic management of diseases which have known or suspected immunologic causes, such as diseases which are caused by abnormal rise in immunological function. Thus, the compositions of the invention are useful for the treatment of various connective tissue diseases including but not limited to systemic lupus erythematosus, arthritis (including but not limited to rheumatoid arthritis); treatment of renal disease including but not limited to glomerulonephritides (post-streptococcal or other) and tubulo-interstitial nephritis. It is to be understood that the uses of the compositions of this invention as set forth herein are exemplary only and that they do not limit the scope or practice of the invention.

The immunomodulatory, or more specifically, for example, the immunosuppressive activity of the compositions of the invention can be and has been demonstrated utilizing the procedures which follow.

Immunosuppressive Activity of Vitamin D compounds on cytotoxic T lymphocyte Responses-General Test Description Cytotoxic thymus-derived lymphocytes (CTL) constitute an important aspect of immune function and, as a result, play a key role in the rejection of grafted cells, tissues and organs. It is, therefore, essential to suppress CTL generation in a clinical situation in which CTL function is antithetical to the desired outcome as, for example, in transplantation. Cytotoxic T-lymphocytes have been studied for several years by many investigators and methods to evaluate CTL responses in vitro are well established.

As described below, CTL responses as affected by Vitamin D derivatives, were studied in vitro using cells from lab animals and human volunteers. Cytotoxic T-lymphocytes were generated from responder lymphoid cells in tissue culture medium during an incubation period of 6 days by exposure to foreign stimulator cells, i.e. from a genetically disparate source. A portion of the resultant effector cells were CTL capable of killing fresh cells related to the stimulator cells employed in the 6 day culture. To detect killing of cells by CTL, fresh target cells were incubated in excess [51]chromium (as sodium chromate) until they were extensively labelled. Since target cells will retain the internalized radioisotope as long as they are viable but release the label when they are killed, CTL activity was assessed by quantitating the chromium released from target cells after a 4 or 18 hour incubation with CTL. Immunosuppression produced by Vitamin D derivatives was gauged as the ability to inhibit CTL responses during the initial incubation period relative to control cultures to which no Vitamin D derivative was added.

Murine Test Methods

Mice

Female BALB/c By and C57BL/6 mice were obtained from Jackson Laboratories and were used between 8 and 10 weeks of age. Mice were given food and water ad libitum and were kept in a 12 hour light and 12 hour dark cycle.

Murine Tissue Culture Medium

For murine cultures, minimal essential medium with Hank's salts was supplemented to 1 millimolar with sodium pyruvate, to 0.1 millimolar with nonessential amino acids, to 2 millimolar with l-glutamine, to 10% (v/v) with heat-inactivated fetal bovine serum, to 50 micrograms per ml with gentamicin, and to 1000 milligrams per liter with sodium bicarbonate and was used as tissue culture medium.

Solutions of Vitamin D Derivatives

Stock solutions of Vitamin D derivatives were made in argon-saturated ethanol at a final concentration of $1 \times 10^{-2}$ molar, were covered with argon before sealing and were stored at $-20°$ C. in the dark. Reduced lighting conditions were always employed when working with compounds. Compounds were diluted in tissue culture medium to $1 \times 10^{-4}$ molar and all subsequent dilutions were done in tissue culture medium containing 1% v/v ethanol. The final dilution into culture vessels was 1:10 thus keeping the vehicle concentration constant at 0.1% while varying the concentration of compound as tabulated in the results. For purposes of control, mixed leukocyte cultures were incubated in medium only (medium control) or in medium containing a final concentration of 0.1% ethanol (vehicle control).

Generation of Cytotoxic T-lymphocytes

Murine cytotoxic T-lymphocytes were generated in mixed leukocyte cultures by known methods. Specifically, single cell suspensions were prepared from spleens by gentle disruption in balanced salt solution (Hanks' balanced salt solution supplemented to 10%, v/v, with fetal bovine serum). After sedimentation on ice to remove particulate debris, cell suspensions were centrifuged at 400xg and were resuspended in fresh balanced salt solution. Cells to be used as stimulator cells were precluded from proliferating or generating cytotoxic T-lymphocytes by exposure to 1000 rads of gamma irradiation using a $^{137}$cesium source. After washing, spleen cells were resuspended in tissue culture medium and viability was determined by standard trypan blue dye exclusion methodology; 0.1 ml of cells and 0.02 ml of 0.4% trypan blue were mixed, 0.08 ml of 1% acetic acid in water was added and, using light microscopy, viable cells were determined as having excluded dye while dead cells were stained blue. Cells were diluted to the desired concentration and mixed leukocyte cultures were established in 16 mm tissue culture wells at a final volume of 2.0 ml per well containing $7 \times 10^6$ responder (BALB/c By) and $1 \times 10^6$ irradiation-inactivated stimulator (C57BL/6) cells. Unless otherwise indicated, mixed leukocyte cultures were incubated at 37° C. for 6 days in a humidified atmosphere of 5% $CO_2$ in air.

Target Cells for the Cytotoxic T-lymphocyte Assays

Target cells for the murine cytotoxic T-lymphocyte assay were EL-4 lymphoma cells which are syngeneic with C57BL/6 mice and therefore express the same major transplantation antigens. The EL-4 tumor cells were maintained by serial passage in tissue culture medium. Five to ten million tumor cells were suspended in 1.0 ml of tissue culture medium containing 250 microcuries of $^{51}$chromium ($^{51}$Cr) as sodium chromate (specific activity 200–900 curies per gram) and were incubated 3–4 h at 37° C. Radiolabelled target cells were subsequently washed three times through 1.0 ml aliquots of fetal bovine serum to remove unbound $^{51}$Cr and adjusted to $1 \times 10^5$ per ml with tissue culture medium.

Cytotoxic T-lymphocyte Assays

The murine cytotoxic T-lymphocyte assay was conducted as follows. Cells from mixed leukocyte culture were collected by aspiration and were sedimented at 400xg for 10 minutes at 4° C. Cell pellets were resuspended in tissue culture medium and viable cells were enumerated by microscopy after exposure to trypan blue. Percent viability was calculated according to the formula:

$$\text{Cell viability (\%)} = 100 \times \frac{\text{number of viable cells counted}}{\text{total cells counted}}.$$

Viable effector cells were adjusted to the desired concentration in tissue culture medium and added to an equal volume (0.1 ml) of the $^{51}$Cr labelled target cell suspension in round bottom wells of a 96-well microtest plate. Triplicate wells containing effector cells and target cells were incubated for 4 hours at 37° in a humidified atmosphere of 5% $CO_2$ in air. One-tenth ml of cell-free supernatant fluid was collected from each well and transferred to a $5 \times 60$ mm tube and radioactivity in the supernatant fluid was measured in a gamma spectrometer. Spontaneous release of $^{51}$Cr was measured from target cells incubated alone and maximal release of $^{51}$Cr was defined as the radioactivity released from target cells after three cycles of freezing and thawing. The cytotoxic T-lymphocyte activity generated in any mixed leukocyte culture is expressed as CTL activity or percentage of specific $^{51}$Cr release (% specific $^{51}$Cr release) calculated according to the formula:

$$100 \times \left( \frac{\text{experimental release (c.p.m.)} - \text{spontaneous release (c.p.m.)}}{\text{maximal release (c.p.m.)} - \text{spontaneous release (c.p.m.)}} \right)$$

Suppression of cytotoxic T-lymphocyte responses is presented as percent inhibition of CTL activity (Inhibition of CTL activity (%)) and was calculated according to the formula:

$$100 \times \left( 1 - \frac{\text{CTL activity in experimental cultures}}{\text{CTL activity in control cultures}} \right)$$

Effect of Vitamin D Derivatives on Cytotoxic T-lymphocyte Responses

During the mixed leukocyte culture phase of the murine tests, three each of medium control and vehicle control cultures were included; each being assayed separately for cell viability and CTL activity. Unless otherwise indicated, single cultures were used to test for the effect of a particular concentration of any Vitamin D derivative. Moreover, cell viability was generally assessed only from control cultures; the resultant mean values being used to prepare desired viable effector cell concentrations from all cultures. The results for control cultures are expressed as the mean from replicate mixed leukocyte cultures±standard deviation thus establishing the between-culture variability inherent to any particular experiment. That changes in CTL activity were compound-induced was evidenced by dose-dependent changes in CTL activity measured from single cultures which exceeded the variability of the test system. That such compound-induced changes in CTL activity owe to relevant immunomodulatory mechanisms and not to frank toxicity was demonstrated in separate experiments.

RESULTS

As can be seen in Table I 1α,25-dihydroxyergocalciferol, 1α,25-dihydroxycholecalciferol-26,23-lactone; and 1α,23S,25 trihydroxycholecalciferol suppress murine cytotoxic T-lymphocyte responses.

TABLE I
IMMUNOSUPPRESSION BY VITAMIN D DERIVATIVES: INHIBITION OF MURINE CYTOTOXIC T-LYMPHOCYTE RESPONSES, IN VITRO.

| Compound and concentration (molar) | CTL activity[a] (% specific $^{51}$Cr release) | Inhibition of CTL activity (%) |
|---|---|---|
| No compound or[b] vehicle, (medium control) | 56.3 ± 3.1 | — |
| Vehicle control[b] (0.1% ethanol) | 53.7 ± 1.5 | 0 |
| 1α,25-(OH)$_2$[c]—D$_2$ | | |
| $1 \times 10^{-10}$ | 52 | 3 |
| $1 \times 10^{-9}$ | 43 | 20 |
| $1 \times 10^{-8}$ | 32 | 40 |
| $1 \times 10^{-7}$ | 28 | 48 |
| $1 \times 10^{-6}$ | 20 | 63 |
| $1 \times 10^{-5}$ | 5 | 91 |
| 1α,25-(OH)$_2$[c]—D$_3$-(26,23)-lactone | | |
| $1 \times 10^{-10}$ | 50 | 7 |
| $1 \times 10^{-9}$ | 52 | 3 |
| $1 \times 10^{-8}$ | 49 | 9 |
| $1 \times 10^{-7}$ | 34 | 37 |
| $1 \times 10^{-6}$ | 20 | 63 |
| $1 \times 10^{-5}$ | 11 | 80 |
| No compound or[b] vehicle (medium control) | not done | — |

TABLE I-continued
IMMUNOSUPPRESSION BY VITAMIN D DERIVATIVES: INHIBITION OF MURINE CYTOTOXIC T-LYMPHOCYTE RESPONSES, IN VITRO.

| Compound and concentration (molar) | CTL activity[a] (% specific $^{51}$Cr release) | Inhibition of CTL activity (%) |
|---|---|---|
| Vehicle control[b] (0.1% ethanol) | 43.7 ± 7.6 | 0 |
| 1α,23S,25-[c](OH)$_3$—D$_3$ | | |
| $1 \times 10^{-9}$ | 45 | 0 |
| $1 \times 10^{-8}$ | 36 | 18 |
| $1 \times 10^{-7}$ | 25 | 43 |
| $1 \times 10^{-6}$ | 18 | 59 |
| $1 \times 10^{-5}$ | 10 | 77 |

Footnotes to Table I
[a]The $^{51}$Cr release assay was done in triplicate for each culture at a 90:1 effector to target cell ratio based on viable cell yields from control cultures. Results are expressed as the mean CTL activity ± S.D. of three cultures for each control and as the mean $^{51}$Cr release produced by cells from single test cultures. (See Specific Test Methods Section Above).
[b]Control cultures consist of cells incubated in tissue culture medium only (medium control) or in tissue culture medium plus vehicle (vehicle control). The test cultures just below, consist of cells incubated in tissue culture medium and vehicle plus the molar concentration of vitamin D compounds as shown. Vehicle (ethanol) was included in all test cultures at 0.1%, v/v. The rest of the tables in this specification are similarly arranged.
[c]1α,25-(OH)$_2$—D$_2$ is 1α,25-dihydroxyergocalciferol; 1α,25-(OH)$_2$—D$_3$-(26,23)-lactone is 1α,25-dihydroxycholecalciferol-26,23-lactone and 1α,23S,25-(OH)$_3$—D$_3$ is 1α,23S,25-trihydroxycholecalciferol. These abbreviations for these compound names are used throughout the specification.

RESULTS

While the methods employed in previous studies established that cytotoxic T-lymphocyte responses were inhibited by various vitamin D derivatives, they did not establish whether or not the inhibition was due to direct toxicity of the compounds on cultured cells. The data shown in Table II below address this point. Specifically, Table II shows that immunosuppressive concentrations of 1α,25-dihydroxyergocalciferol are not toxic to cultured murine cells.

TABLE II
IMMUNOSUPPRESSIVE CONCENTRATIONS OF 1α,25-DIHYDROXYERGOCALCIFEROL ARE NOT TOXIC TO CULTURED CELLS.

| Compound and concentration (molar) | CTL activity[a] (% specific $^{51}$Cr release) | Inhibition of CTL activity (%) | Cell[b] viability (%) | Total viable[b] cells recovered ($\times 10^{-6}$) |
|---|---|---|---|---|
| No compound or[c] vehicle, medium only | 53.7 ± 6.7 | — | not done | not done |
| Vehicle (0.1% ethanol)[c] | 47.3 ± 4.1 | 0 | 55.3 ± 1.2 | 5.19 ± 0.34 |
| 1α,25-(OH)$_2$—D$_2$[d] | | | | |
| $1 \times 10^{-10}$ | 38 | 20 | 57 | 5.84 |
| $1 \times 10^{-9}$ | 38 | 20 | 58 | 5.96 |
| $1 \times 10^{-8}$ | 30 | 37 | 57 | 5.64 |
| $1 \times 10^{-7}$ | 21 | 56 | 57 | 5.04 |
| $1 \times 10^{-6}$ | 21 | 56 | 57 | 5.20 |

Footnotes to Table II
[a]The $^{51}$Cr release assay was done in triplicate for each culture at a 90:1 effector to target cell ratio based on viable cell yields from control cultures. Results are expressed as the mean CTL activity ± S.D. of three cultures for each control and as the mean $^{51}$Cr release produced by cells from single test cultures (see Specific Test Methods section above).
[b]The viability of cells from each culture was determined by trypan blue dye exclusion. Results are expressed as the mean % viability or total viable cells recovered ± S.D. of three cultures for each control or as the value determined for each single test culture.
[c]See footnote b, Table I.
[d]See footnote c, Table I.

Suppression of murine CTL responses in vivo by treatment of mice with 22,23-dehydro-1α,25S,26-trihydroxycholecalciferol.

General description. The general test considerations are similar to those previously described for the in vitro murine experiments except that stimulator cells and experimental compound were administered to intact laboratory mice. The impact of compound on CTL responses generated in vivo was determined by comparing the resultant CTL activity from test mice to the CTL activity generated in mice which received vehicle only.

Specific procedures for in vivo experiments

Female C57BL/6 mice were used between the ages of 9-12 weeks. Mice were given food and water ad libitum and were kept in a 12-hour light and 12-hour dark cycle.

A balanced salt solution (BSS) was prepared as described for tissue culture medium in the in vitro murine experiments but was additionally supplemented to 0.01 molar with HEPES buffer.

The compound, 22,23-dehydro-1α,25S,26-trihydroxycholecalciferol was dissolved in dimethylsulfoxide at final concentrations of 2 or 4 mg per ml. When working with vitamin D compounds, conditions of reduced lighting were employed.

In vivo regimens. Mice were apportioned at 4 per group and were inoculated intraperitoneally with $3 \times 10^6$ allogeneic P815 tumor cells and the resulting CTL activity was assessed 10 days later. Mice were treated by the intraperitoneal route with 25 microliters of test compound dissolved in dimethylsulfoxide or with dimethylsulfoxide only (vehicle control). In test 1, mice were given daily treatments of 50 micrograms of 22,23-dehydro-1α,25S,26-trihydroxycholecalciferol per day starting one day before immunization and continuing until the day before assay. In test 2, mice were treated with 100 micrograms of 22,23-dehydro-1α,25S,26-trihydroxycholecalciferol only twice: on the day before immunization and on the day of immunization.

Assay for CTL activity. Ten days after immunization of mice with P815 cells, single spleen cell suspensions were prepared by passage of spleens through a steel mesh into BSS and were subsequently washed twice with BSS. Further manipulations of spleen cells, labeling of P815 target cells with $^{51}$Cr, mechanics of the assay, and the calculation of results from the CTL assay are the same as described earlier for the in vitro murine CTL tests. Cytotoxic T lymphocyte activity was determined individually on spleen cells from each animal in each group and the results are expressed as the mean CTL activity (as percent specific $^{51}$Cr release) of each group±the standard deviation.

Statistical analysis. A student's t-test was to compare the vehicle-treated group to the test group in each test and the resultant p values are shown.

RESULTS

As shown in Table III, mice immunized with P815 cells developed substantially CTL activity within 10 days in the vehicle control groups. A statistically significant reduction in CTL activity was seen in both tests in those groups which had been treated with 22,23-dehydro-1α,25S,26-trihydroxycholecalciferol thus documenting the immunosuppressive activity of the compound when administered to animals.

TABLE III

SUPPRESSION OF CYTOTOXIC T-LYMPHOCYTE RESPONSES, IN VIVO, BY TREATMENT WITH 22 23-DEHYDRO-1α,25S,26-TRIHYDROXYCHOLECALCIFEROL

| Test #[a] | Treatment | CTL activity (% specific $^{51}$Cr release)[b] | Inhibition of CTL activity (%) |
|---|---|---|---|
| 1 | vehicle control | 31 ± 5 | — |
|  | 1α,25S,26-(OH)$_3$—Δ$^{22}$-D$_3$[c] (50 ug/dose) | 13 ± 4 | 58 p < 0.05 |
| 2 | vehicle control | 30 ± 3 | — |
|  | 1α,25S,26-(OH)$_3$—Δ$^{22}$-D$_3$[c] (100 ug/dose) | 14 ± 2 | 53 p < 0.01 |

Footnotes to TABLE III
[a]In test 1, animals were treated daily with compound or vehicle starting 1 day before immunization and continuing until the day before assay. In test 2, animals were treated only twice, one day before immunization and on the day of immunization.
[b]The effector to target cell ratio used in both tests was 10:1. Data at 20:1 and 40:1 effector to target cell ratios revealed an identical pattern of results.
[c]1α,25S,26-(OH)$_3$-Δ$^{22}$-D$_3$ is 22,23-dehydro-1α,25S,26-trihydroxycholecalciferol.

Specific Methods for Tests on Human Cells

Human Cells

Human cells for the tests described below were taken from four donors designated I, II, III, and IV in the tables below.

Tissue Culture Medium for Human Cells

Tissue culture medium for human mixed leukocyte-tumor cultures was a 1:1 mixture of RPMI 1640 and Dulbecco's modified Eagle's medium supplemented to 2 millimolar with 1-glutamine, to 100 units per ml with penicillin, to 100 micrograms per ml with streptomycin, to 0.1 millimolar with nonessential amino acids, to 0.5 millimolar with arginine hydrogen chloride, and to 5% with human AB serum.

Solutions of Vitamin D Derivatives

Stock solutions of Vitamin D derivatives were prepared as they were prepared above in the murine tests.

Generation of Cytotoxic T-lymphocytes

Human cytotoxic T-lymphocytes were generated in mixed leukocyte-tumor cultures by known methods. Specifically, blood from normal volunteer donors was drawn into heparinized syringes, diluted 1:1 with calcium-magnesium free Hanks' balanced salt solution (Ca-Mg free HBSS), and layered over lymphocyte separation medium (Litton Bionetics, Kensington, MD). After centrifugation at 500xg for 20-30 min at room temperature, peripheral blood mononuclear cells were harvested from the interface. The peripheral blood mononuclear leukocytes were centrifuged and resuspended in Ca-Mg free HBSS and were subsequently separated from platelets by centrifugation at 500xg through a solution of 20% sucrose and 1% human AB serum in Ca-Mg free HBSS. The cells were washed once and finally resuspended in tissue culture medium. Cells of the human melanoma tumor cell line (HT-144) were used as stimulator cells and were maintained by weekly passage in tissue culture medium. Cells to be used as stimulator cells in mixed leukocyte-tumor cultures were irradiated with 10,000 rads of gamma irradiation to preclude proliferation in culture. Mixed leukocyte-tumor cell cultures were established in 16 mm tissue culture wells at a final volume of 1.5 ml per well containing $2 \times 10^6$ peripheral blood mononuclear leukocytes and $5 \times 10^4$ irradiation-inactivated stimulator cells. In order to prevent the generation of nonspecific cytotoxic cells in these cultures, hydrocortisone sodium succinate was added to each culture at a final concentration of $1 \times 10^{-5}$M. Mixed leukocyte-tumor cultures were incubated for 6 days in a humidified atmosphere of 5% $CO_2$ in air.

Target Cells for the Cytotoxic T-lymphocyte Assays

For assay of human cytotoxic T-lymphocytes, freshly trypsinized HT-144 human melanoma cells were used as targets and were radiolabelled by incubation with 100 microcuries $^{51}Cr$ in 0.5 ml tissue culture medium for 1 hour at 37° C. Labelled target cells were washed free of unbound isotope by 3 serial washes in tissue culture medium and were finally resuspended at a concentration of $5 \times 10^4$ cells per ml.

Cytotoxic T-lymphocyte Assays

Assays of human cytotoxic T-lymphocytes were done by known methods. Specifically, one-tenth ml aliquots of $^{51}Cr$-labelled target cell suspension were added to "half area" microtest plates and were incubated at 37° C. for 18 hours in a humidified atmosphere of 5% $CO_2$ in air to permit the cells to adhere and spread on the floor of each well. Culture medium was then aspirated from each well and was replaced with 0.1 ml of tissue culture medium containing cells harvested from mixed leukocyte-tumor cultures which had been processed as described for murine mixed leukocute cultures, above. Control wells for measurement of spontaneous $^{51}Cr$ release received medium without effector cells and wells for measurement of maximal releasable $^{51}Cr$ received 0.1 ml of 2% sodium dodecyl sulfate in distilled water. After overnight incubation at 37° in a humidified atmosphere of 5% $CO_2$ in air, 0.05 ml of cell-free supernatant was withdrawn from each well and the amount of released $^{51}Cr$ was quantitated using a gamma spectrometer. The percentage of specific $^{51}Cr$ release (CTL activity) and the percent inhibition of CTL activity were calculated with the same formulas used above for the murine CTL assay.

Human Cell Experiments

Effect of Vitamin D Derivatives on Cytotoxic T-lymphocyte Responses

Tests conducted on human cytotoxic T-lymphocyte responses are reported as the mean±standard error of the mean from triplicate $^{51}Cr$ release determinations on pooled cells from duplicate control or test cultures. Consistent or dose-dependent inhibition of CTL responses, in the absence of reduced cell viability, demonstrated compound-induced immunosuppression. The Results Section and the Table IV which follow give the results of the human cell tests.

RESULTS

As can be seen in Table IV, non-toxic concentrations of 1α,23S,25-trihydroxycholecalciferol suppressed the generation of human cytotoxic T-lymphocytes.

Similar results were obtained for 22,23-dehydro-1α,25S,26-trihydroxycholecalciferol; 24R-fluoro-1α,25-dihydroxycholecalciferol; 24,24-difluoro-1α,25-dihydroxycholecaliciferol; 5,6-trans-1α,25-dihydroxycholecalciferol; 1α,25S,26-trihydroxyergocalciferol; 26,26,26,27,27,27-hexafluoro-1α,25dihydroxycholdcalciferol; and 22,23-dehydro-26,26,26,27,27,27-hexafluoro-1α,25-dihydroycholecalciferol as can also be seen in Table IV.

TABLE IV

IMMUNOMODULATORY ACTIVITY OF VITAMIN D COMPOUNDS: INHIBITION OF HUMAN CTL RESPONSES.

Contents of mixed leukocyte-tumor cultures[a]

| leukocytes from donors I, II, III or IV | HT-144 melanoma cells | Identity and molar concentration of Vitamin D Compounds | Total viable cells recovered ($\times 10^{-6}$) | CTL[b] activity (% specific $^{51}Cr$ release) | Inhibition of CTL activity (%) |
|---|---|---|---|---|---|
| Test 1 | | 1α,23S,25-(OH)$_3$—D$_3$[c] | | | |
| I | — | vehicle control (0.1% ethanol) | 2.4 | 0 ± 5 | — |
| I | + | vehicle control (0.1% ethanol) | 2.4 | 43 ± 4 | 0 |
| I | + | $1 \times 10^{-6}$ | 2.2 | 12 ± 3 | 72 |
| I | + | $1 \times 10^{-5}$ | 2.6 | 2 ± 3 | 95 |
| Test 2 | | | | | |
| II | — | vehicle control (0.1% ethanol) | 1.5 | −9 ± 12 | — |
| II | + | vehicle control (0.1% ethanol) | 1.7 | 37 ± 8 | 0 |
| II | + | $1 \times 10^{-7}$ | 1.7 | 10 ± 2 | 73 |
| II | + | $1 \times 10^{-6}$ | 1.5 | 14 ± 7 | 62 |
| Test 1 | | 1α,25S,26-(OH)$_3$—Δ$^{22}$-D$_3$[c] | | | |
| I | — | vehicle control (0.1% ethanol) | 2.4 | 0 ± 5 | — |
| I | + | vehicle control (0.1% ethanol) | 2.4 | 43 ± 4 | 0 |
| I | + | $1 \times 10^{-6}$ | 1.8 | 13 ± 8 | 70 |
| I | + | $1 \times 10^{-5}$ | 2.0 | 16 ± 4 | 63 |
| Test 2 | | | | | |
| II | — | vehicle control (0.1% ethanol) | 1.5 | −9 ± 12 | — |
| II | + | vehicle control (0.1% ethanol) | 1.7 | 37 ± 8 | 0 |
| II | + | $1 \times 10^{-7}$ | 1.3 | 1 ± 4 | 97 |
| II | + | $1 \times 10^{-6}$ | 1.2 | 19 ± 4 | 49 |
| Test 1 | | 24R-F—1α,25-(OH)$_2$—D$_3$[c] | | | |
| I | — | vehicle control (0.01% ethanol) | 2.8 | 1 ± 22 | — |
| I | + | vehicle control (0.01% ethanol) | 5.1 | 52 ± 5 | 0 |
| I | + | $1 \times 10^{-7}$ | 3.9 | 20 ± 1 | 62 |
| I | + | $1 \times 10^{-6}$ | 3.6 | 7 ± 6 | 87 |

TABLE IV-continued
IMMUNOMODULATORY ACTIVITY OF VITAMIN D COMPOUNDS: INHIBITION OF HUMAN CTL RESPONSES.

| leukocytes from donors I, II, III or IV | HT-144 melanoma cells | Identity and molar concentration of Vitamin D Compounds | Total viable cells recovered ($\times 10^{-6}$) | CTL[b] activity (% specific $^{51}$Cr release) | Inhibition of CTL activity (%) |
|---|---|---|---|---|---|
| Test 2 | | | | | |
| I | − | vehicle control (0.01% ethanol) | 1.1 | −10 ± 2 | — |
| I | + | vehicle control (0.01% ethanol) | 1.9 | 54 ± 3 | 0 |
| I | + | 1 × 10$^{-6}$ | 1.2 | 0 ± 3 | 100 |
| I | + | 1 × 10$^{-5}$ | 1.2 | 3 ± 4 | 94 |
| Test 1 | | 24,24-(F)$_2$—1α,25-(OH)$_2$—D$_3$[c] | | | |
| I | − | vehicle control (0.01% ethanol) | 2.8 | 1 ± 2 | — |
| I | + | vehicle control (0.01% ethanol) | 5.1 | 52 ± 5 | 0 |
| I | + | 1 × 10$^{-7}$ | 5.3 | 10 ± 1 | 81 |
| I | + | 1 × 10$^{-6}$ | 3.5 | 15 ± 1 | 71 |
| Test 2 | | | | | |
| I | − | vehicle control (0.01% ethanol) | 1.1 | −10 ± 2 | — |
| I | + | vehicle control (0.01% ethanol) | 1.9 | 54 ± 3 | 0 |
| I | + | 1 × 10$^{-6}$ | 1.4 | 5 ± 2 | 91 |
| I | + | 1 × 10$^{-5}$ | 1.5 | 9 ± 2 | 83 |
| Test 1 | | 5,6-trans-1α,25-(OH)$_2$—D$_3$[c] | | | |
| I | − | vehicle control (0.01% ethanol) | 2.8 | 1 ± 2 | — |
| I | + | vehicle control (0.01% ethanol) | 5.1 | 52 ± 5 | 0 |
| I | + | 1 × 10$^{-7}$ | 4.3 | 20 ± 2 | 62 |
| I | + | 1 × 10$^{-6}$ | 4.1 | 20 ± 2 | 62 |
| Test 2 | | | | | |
| I | − | vehicle control (0.01% ethanol) | 2.4 | 0 ± 5 | — |
| I | + | vehicle control (0.01% ethanol) | 2.4 | 43 ± 4 | 0 |
| I | + | 1 × 10$^{-6}$ | 2.2 | 11 ± 2 | 74 |
| I | + | 1 × 10$^{-5}$ | 2.2 | 17 ± 3 | 60 |
| Test 1 | | 1α,25S,26-(OH)$_3$—D$_2$[c] | | | |
| I | − | vehicle control (0.1% ethanol) | 2.6 | 2 ± 2 | — |
| I | + | vehicle control (0.1% ethanol) | 3.3 | 37 ± 3 | 0 |
| I | + | 1 × 10$^{-7}$ | 3.0 | 9 ± 2 | 76 |
| I | + | 1 × 10$^{-6}$ | 2.9 | 17 ± 4 | 54 |
| Test 2 | | | | | |
| III | − | vehicle control (0.1% ethanol) | 1.8 | 1 ± 5 | — |
| III | + | vehicle control (0.1% ethanol) | 2.9 | 54 ± 4 | 0 |
| III | + | 1 × 10$^{-7}$ | 2.2 | 7 ± 2 | 87 |
| III | + | 1 × 10$^{-6}$ | 2.3 | −4 ± 2 | 100 |
| Test 3 | | | | | |
| IV | − | vehicle control (0.1% ethanol) | 1.7 | 4 ± 2 | — |
| IV | + | vehicle control (0.1% ethanol) | 1.7 | 57 ± 1 | 0 |
| IV | + | 1 × 10$^{-7}$ | 1.9 | 34 ± 10 | 40 |
| IV | + | 1 × 10$^{-6}$ | 1.8 | 10 ± 2 | 82 |
| Test 1 | | | | | |
| I | − | Vehicle control (0.1% ethanol) | 1.8 | 0 ± 1 | |
| I | + | Vehicle Control (0.1% ethanol) 26,26,26,27,27,27-(F)$_6$—1α,25-(OH)$_2$—Δ$^{22}$-D$_3$ | 2.0 | 64 ± 3 | |
| I | + | 1 × 10$^{-7}$ | 2.3 | 23 ± 2 | 64 |
| I | + | 1 × 10$^{-6}$ 26,26,26,27,27,27-(F)$_6$—1α,25-(OH)$_2$—D$_3$[c] | 2.3 | 13 ± 0.1 | 80 |
| I | + | 1 × 10$^{-7}$ | 2.8 | 23 ± 3 | 64 |

TABLE IV-continued

IMMUNOMODULATORY ACTIVITY OF VITAMIN D COMPOUNDS:
INHIBITION OF HUMAN CTL RESPONSES.
Contents of mixed leukocyte-tumor cultures[a]

| leukocytes from donors I, II, III or IV | HT-144 melanoma cells | Identity and molar concentration of Vitamin D Compounds | Total viable cells recovered ($\times 10^{-6}$) | CTL[b] activity (% specific $^{51}Cr$ release) | Inhibition of CTL activity (%) |
|---|---|---|---|---|---|
| I | + | $1 \times 10^{-6}$ | 2.4 | 15 ± 2 | 77 |

Footnotes to TABLE IV

[a] Mixed leukoctye-tumor cultures were incubated for 6 days. For each test, cultures designated "vehicle control" consist of cells incubated in tissue culture medium plus vehicle (ethanol) at the concentrations shown. Test cultures, just below, consist of cells incubated in tissue culture medium and vehicle plus the molar concentration of vitamin D compounds indicated.

[b] Cells from replicate cultures were pooled and assayed in triplicate for CTL activity using the $^{51}Cr$-release assay. Results are expressed as the mean % $^{51}Cr$-release ± S.E.M. Effector to target cell ratios were 32:1 for lymphocytes from donor III in test 1 testing $1\alpha,25S,26\text{-}(OH)_3\text{--}D_2$; 24:1 for lymphocytes from donor IV in test 2 testing $1\alpha,25S,26\text{-}(OH)_3\text{--}D_2$; 8:1 for lymphocytes in test 1 testing $26,26,26,27,27,27\text{-}(F)_6\text{--}1\alpha,25\text{-}(OH)_2\text{--}D_3$ and $26,26,26,27,27,27\text{-}(F)_6\text{--}1\alpha,25\text{-}(OH)_2\text{--}\Delta^{22}\text{-}D_3$ and 6:1 in all other experiments.

[c] $1\alpha,23S,25\text{-}(OH)_3\text{--}\Delta^{22}\text{-}D_3$ is 22,23-dehydro-$1\alpha$, 25S,26-trihydroxycholecalciferol, 24R-F--$1\alpha,25\text{-}(OH)_2\text{--}D_3$ is 24R-fluoro-$1\alpha,25$-dihydroxycholecalciferol, 24,24-$(F)_2\text{--}1\alpha,25\text{-}(OH)_2\text{--}D_3$ is 24,24-difluoro-$1\alpha,25$-dihydroxycholecalciferol, 5,6-trans-$1\alpha,25$-$(OH)_2\text{--}D_3$ is 5,6 trans-$1\alpha,25$-dihydroxycholecalciferol, $1\alpha,25S,26\text{-}(OH)_3\text{--}D_2$ is $1\alpha,25S,26$-trihydroxyergocalciferol, $26,26,26,27,27,27\text{-}(F)_6\text{--}1\alpha,25\text{-}(OH)_2\text{--}D_3$ is $26,26,26,27,27,27$-hexafluoro-$1\alpha,25$-dihydroxycholecalciferol; $26,26,26,27,27,27\text{-}(F)_6\text{--}1\alpha,25\text{-}\Delta^{22}\text{-}D_3$ is 22,23-dehydro-$26,26,26,27,27,27$-hexafluoro-$1\alpha,25$-dihydroxycholecalciferol.

Immunosuppressive activity of vitamin D compounds on immunoglobulin (antibody) production by human lymphocytes.

General Test Description Humoral immunity comprises one of the two major arms of the immune system and generally is beneficial. However, a number of disease states are characterized by a hyperactive immune system responding to self tissue antigens. Thus, diseases such as rheumatoid arthritis and systemic lupus erythematosis possess an autoimmune component which invariably contributes to pathologic sequelae. In these diseases it would be important to suppress the humoral immune system.

In the following studies we used established methods to examine the effect of Vitamin D derivatives on the in vitro production of immunoglobulin (Ig) by human peripheral blood leukocytes (PBL) following polyclonal activation. Immunoglobulin was induced from PBL by co-culturing the PBL with the polyclonal B cell activator *Staphylococcus aureus* strain Cowan I (SAC) for a period of 8 days. The quantity of Ig produced in the culture supernatants was determined by using an enzyme linked immunosorbent assay (ELISA). The effect of Vitamin D derivatives was determined by comparing the amount of antibody produced in cultures containing Vitamin D derivatives to those cultures containing an appropriate concentration of vehicle (ethanol).

Specific Methods for Examining Effects of Vitamin D derivatives on Human Ig Production Solutions of vitamin D derivatives. Stock solutions of vitamin D derivatives were prepared as described previously for the murine CTL experiments.

INDUCTION OF HUMAN IG SECRETION Human peripheral blood mononuclear leukocytes were prepared from one day old buffy coat preparations obtained from the American Red Cross (Lansing, MI). Cells in the buffy coat suspension were diluted 1:2 with RPMI 1640 medium. Twenty five ml of this preparation were overlayed onto 25 ml of Ficoll-Paque contained in a 50 ml polypropylene centrifuge tube. After centrifugation at 400×g at 15° C. for 40 min, the cells at the interface of the medium and Ficoll were removed and washed 3 times in 50 ml RPMI medium and centrifuged at 300×g for 10 minutes. After the final centrifugation, the cell pellet was suspended in RPMI medium containing 20% fetal bovine serum (FBS) and 80 µg/ml gentamicin. The number of viable cells was determined by trypan blue exclusion and were then suspended to $2.5 \times 10^6$ viable cells per ml in RPMI containing 20% FBS and gentamicin. Human PBL were induced to secrete Ig as follows. One hundred microliters of the PBL suspension and an additional 100 µl of a 1:20,000 (v/v) preparation of SAC suspended in RPMI containing 1% FBS were added to each well of a 96-well microtiter plate. Selected wells were also set up without the addition of SAC to serve as negative controls (spontaneous Ig secretion). Each well then received 20 µl of either the appropriate dilution of Vitamin D derivative in RPMI with 1% ethanol or RPMI with 1% ethanol (vehicle control). The vitamin D derivatives were tested at final concentrations of $10^{-5}$, $10^{-6}$, $10^{-7}$, $10^{-8}$, $10^{-9}$, and $10^{-10}$M and in all cases the vehicle (ethanol) concentration was 0.1%. All treatments were performed in triplicate. Following incubation of the culture plates for 8 days at 37° C. in a humidified atmosphere containing 5% $CO_2$, 95% air, 150 µl of culture supernatant were removed from each well and transferred to a separate 96 well plate. The samples were then either assayed immediately or stored at −20° C. until assayed by the ELISA technique described below.

QUANTITATION OF SECRETED IG (ELISA ASSAY) ELISA plates were prepared for quantitating human IgG and IgM levels in culture supernatants as follows. Affinity purified sheep anti-human IgG and goat anti-human IgM (Cappel, Cochranville, PA) were diluted 1:250 and 1:400 respectively, in carbonate coating buffer (0.05M sodium bicarbonate, 0.05M sodium carbonate, 0.15M sodium chloride). One hundred and fifty microliters of the antibody preparation were added to each well of a 96 well ELISA plate (EIA, Costar). The plates were sealed and incubated overnight at 4° C. and on the following day were washed 3 times with distilled water. Each well then received 350 µl of Dulbecco's PBS containing 1 mg/ml bovine serum albumin (BSA) and 0.5 mg/ml sodium azide. The plates were allowed to incubate for 1 hour at 37° C. and then washed 3 times with Dulbecco's PBS containing 0.5% stock Tween 20 (PBS-Tween) followed by 2 washes with distilled water. The plates were air dried and stored desiccated under a vacuum at 4° C. until use.

Samples for Ig quantitation were diluted either 1:2 or 1:4 in Dulbecco's PBS containing 1 mg/ml BSA, 0.5M NaCl, 0.5% stock Tween 20 and 0.5 mg/ml sodium azide (diluting buffer) and 100 µl of each were added to individual wells of the ELISA plate. In addition, a series of dilutions of a standard preparation of human IgG and IgM were included in each ELISA assay in order to generate a standard curve for quantitating Ig levels (see below). The plates were incubated on a shaker at ambient temperature for 15 minutes and then washed 3 times with PBS-Tween.

Alkaline phosphatase conjugated goat anti-human IgG or IgM (Sigma) was diluted 1:1000 in diluting buffer, one hundred microliters were added to each well, and the plates were incubated overnight, in the dark, at 4° C. The plates were then washed 4 times with distilled water followed by 5 washed with PBS-Tween and 4 washes with distilled water. A solution of p-nitrophenyl phosphate disodium was prepared by adding 1 mg Sigma 104 phosphatase substrate per ml of carbonate coating buffer and one hundred and seventy five microliters of substrate were added to each well. The plates were then incubated on a shaker at room temperature. After the color developed, the enzyme reaction was stopped by adding 25 $\mu$l 3N NaOH to each well. The plates were then agitated on a shaker for an additional 10 minutes and subsequently read on a Titertek Multiskan MC at 405 nm.

The optical density (O.D.) determinations were converted into micrograms of IgG or IgM by interpolating the mean of each of the triplicate determinations onto an IgG or IgM standard curve. This standard curve was generated by plotting micrograms Ig vs O.D. obtained from the serial dilutions of a known quantity of IgG or IgM that was included with each ELISA assay. In some instances this data was determined by extrapolation since the O.D. readings for experimental samples were either greater or less than the readings obtained for points included within the standard curve. The number of micrograms of antibody determined for the sample was then converted to a value of micrograms Ig per culture well by multiplying the value by the reciprocal of the fraction of the culture supernatant volume assayed in the ELISA assay.

The sensitivity of the ELISA assay allows for the detection of greater than 0.004 micrograms of IgG per culture and 0.04 micrograms of IgM per culture. The data are expressed as the number of micrograms of each class of Ig produced per culture well. Since Ig determinations were made for individual wells of triplicate cultures for each treatment, a standard error was obtained for each culture condition.

That changes in Ig production by cultured cells was compound-induced was evidenced by the dose-dependent nature of the reduction of Ig production and is strengthened by the fact that the standard error of the mean of suppressed test cultures did not overlap the standard error of the mean of control cultures.

RESULTS

Each of the vitamin D derivatives tested resulted in a dose-dependent inhibition of IgM and IgG production by human leukocytes as shown in Table V. In several cases the suppression was sufficient to reduce antibody levels to undetectable levels. The inhibition produced by vitamin D derivatives was accomplished at concentrations which were not toxic to cultured cells as shown in previously described studies on murine and human CTL responses.

TABLE V

IMMUNOSUPPRESSION BY VITAMIN D DERIVATIVES: INHIBITION OF IMMUNOGLOBULIN PRODUCTION BY HUMAN LYMPHOCYTES, IN VITRO.

| Compound and concentration (molar) | IgM[a] $\mu$g per culture (x ± S.E.M.) | IgG[a] $\mu$g per culture (x ± S.E.M.) |
|---|---|---|
| No compound or vehicle[b] (medium control) | 3.11 ± 0.36 | 0.73 ± 0.14 |
| Vehicle control (0.1% ethanol)[b] | 2.49 ± 0.17 | 0.78 ± 0.09 |
| $1\alpha,23S,25\text{-}(OH)_3\text{-}D_3$[c] | | |
| $1 \times 10^{-10}$ | 4.61 ± 0.73 | 0.54 ± 0.18 |
| $1 \times 10^{-9}$ | 1.55 ± 0.96 | 1.14 ± 0.61 |
| $1 \times 10^{-8}$ | 0.46 ± 0.13 | 0.05 ± 0.01 |
| $1 \times 10^{-7}$ | 0.12 ± 0.07 | 0.02 ± 0.002 |
| $1 \times 10^{-6}$ | undetectable[d] | 0.01 ± 0.002 |
| $5,6\text{-trans-}1\alpha,25\text{-}(OH)_2\text{-}D_3$[c] | | |
| $1 \times 10^{-10}$ | 2.79 ± 0.18 | 0.55 ± 0.16 |
| $1 \times 10^{-9}$ | 2.36 ± 0.27 | 0.29 ± 0.05 |
| $1 \times 10^{-8}$ | 0.50 ± 0.21 | 0.21 ± 0.12 |
| $1 \times 10^{-7}$ | 0.04 ± 0.01 | 0.01 ± 0.001 |
| $1 \times 10^{-6}$ | undetectable[d] | undetectable[d] |
| $1\alpha,25S,26\text{-}(OH)_3\text{-}\Delta^{22}\text{-}D_3$[c] | | |
| $1 \times 10^{-10}$ | 1.02 ± 0.34 | 0.20 ± 0.03 |
| $1 \times 10^{-9}$ | 0.24 ± 0.07 | 0.06 ± 0.03 |
| $1 \times 10^{-8}$ | 0.09 ± 0.04 | 0.04 ± 0.01 |
| $1 \times 10^{-7}$ | 0.05 ± 0.03 | 0.01 ± 0.002 |
| $1 \times 10^{-6}$ | undetectable[d] | 0.005 ± 0.002 |
| $1\alpha\text{-F-}25\text{-OH-}D_3$[c] | | |
| $1 \times 10^{-10}$ | 4.48 ± 0.75 | 0.45 ± 0.11 |
| $1 \times 10^{-9}$ | 3.10 ± 0.10 | 0.18 ± 0.001 |
| $1 \times 10^{-8}$ | 1.83 ± 0.29 | 0.14 ± 0.05 |
| $1 \times 10^{-7}$ | 0.38 ± 0.30 | 0.08 ± 0.05 |
| $1 \times 10^{-6}$ | undetectable[d] | undetectable[d] |
| $24R\text{-F-}1\alpha,25\text{-}(OH)_2\text{-}D_3$[c] | | |
| $1 \times 10^{-10}$ | 3.84 ± 0.72 | 0.21 ± 0.06 |
| $1 \times 10^{-9}$ | 3.13 ± 0.41 | 0.22 ± 0.05 |
| $1 \times 10^{-8}$ | 1.23 ± 0.03 | 0.10 ± 0.02 |
| $1 \times 10^{-7}$ | 0.12 ± 0.06 | 0.01 ± 0.002 |
| $1 \times 10^{-6}$ | undetectable[d] | undetectable[d] |
| $24,24\text{-F}_2\text{-}1\alpha,25\text{-}(OH)_2\text{-}D_3$[c] | | |
| $1 \times 10^{-10}$ | 0.50 ± 0.12 | 0.11 ± 0.03 |
| $1 \times 10^{-9}$ | undetectable[d] | 0.02 ± 0.02 |
| $1 \times 10^{-8}$ | undetectable[d] | 0.01 ± 0.003 |
| $1 \times 10^{-7}$ | undetectable[d] | undetectable[d] |
| $1 \times 10^{-6}$ | undetectable[d] | undetectable[d] |
| $1\alpha,25S,26\text{-}(OH)_3\text{-}D_2$ | | |
| $1 \times 10^{-10}$ | 1.09 ± 0.26 | 0.21 ± 0.06 |
| $1 \times 10^{-9}$ | 0.29 ± 0.17 | 0.08 ± 0.03 |
| $1 \times 10^{-8}$ | 0.14 ± 0.12 | 0.07 ± 0.02 |
| $1 \times 10^{-7}$ | 0.03 ± 0.01 | 0.01 ± 0.005 |
| $1 \times 10^{-6}$ | 0.01 ± 0.006 | undetectable |

[a]Immunoglobulin levels were determined individually on triplicate cultures. Results shown are micrograms of IgM or IgG per culture expressed as the mean ± S.E.M.
[b]See footnote b, TABLE I.
[c]$1\alpha,23S,25\text{-}(OH)_3\text{-}D_3$ is $1\alpha,23S,25$-trihydroxycholecalciferol; 5,6-trans-$1\alpha,25$-$(OH)_2$-$D_3$ is 5,6-trans-$1\alpha,25$-dihydroxycholecalciferol; $1\alpha,25S,26$-$(OH)_3$-$\Delta^{22}$-$D_3$ is 22,23-dehydro-$1\alpha,25S,26$-trihydroxycholecalciferol; $1\alpha$-F-25-OH-$D_3$ is 1-fluoro-25-hydroxycholecalciferol; 24R-F-$1\alpha,25$-$(OH)_2$-$D_3$ is 24R-fluoro-$1\alpha,25$-dihydroxycholecalciferol; 24,24-$F_2$-$1\alpha,25$-$(OH)_2$-$D_3$ is 24,24-difluoro-$1\alpha,25$-dihydroxycholecalciferol; and $1\alpha,25S,26$-$(OH)_3$-$D_2$ is $1\alpha,25S,26$-trihydroxyergocalciferol
[d]Immunoglobulin produced was less than could be measured by the assay according to the sensitivity as described in the methods.

Vitamin D derivatives may be administered to a warm-blooded animal requiring modulation of the immune response, such as, for example, immunosuppression, in dosages that are in the range of 0.05 micrograms/kg to 500 micrograms/kg per day. It is to be understood, however, that the dosages set forth herein are to be adjusted to individual requirements and, therefore, are exemplary only and that they do not, to any extent, limit the scope or practice of the invention. Vitamin D derivatives can be administered orally, but they can also be administered subcutaneously, intramuscularly, intravenously, or intraperitoneally.

More particularly, Vitamin D derivatives can be administered utilizing formulation methods, for example compositions such as tablets, capsules, and the like, or elixirs for oral administration, or in sterile solutions or suspensions for parenteral administration. About 0.05 micrograms to 500 micrograms of a Vitamin D derivative is compounded with a pharmaceutically acceptable vehicle, carrier, excipient, binder, preservative, stabilizer, flavor, and the like, in a unit dosage as called for by accepted pharmaceutical practice. The amount of active substance in the foregoing compositions or preparations is in the range previously indicated.

Illustrative of the adjuvants which may be incorporated into tablets, capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate; a sweetening agent such as sucrose, lactose, or saccharin; and a flavoring agent such as peppermint, oil of wintergreen, or cherry. Various other materials may be present as coatings or to otherwise modify the physical form of the dosage unit. For instance, tablets may be coated with shellac, sugar, or both. A syrup or elixir may contain the active compound, sucrose as a sweetening agent, methyl, and propyl parabens as preservatives, a dye, and a flavoring such as cherry or orange flavor.

Sterile compositions for injection can be formulated according to conventional pharmaceutical practice by dissolving or suspending the active substance in a vehicle, such as water for injection, a naturally-occurring vegetable oil, such as sesame oil, coconut oil, peanut oil, cottonseed oil, and the like, or a synthetic fatty vehicle such as ethyl oleate or the like. Buffers, preservatives, antioxidants and the like can be incorporated as required.

Furthermore, the compositions of the invention may comprise more than one Vitamin D derivative. For example, a composition of the present invention may comprise 1α, 25S, 26-trihydroxy-Δ$^{22}$-cholecalciferol and 1α,25-dihydroxyergocalciferol.

As mentioned earlier, the compositions of the invention, possess immunomodulatory activity, and are therefore useful as immunomodulatory or more specifically, for example, immunosuppressive agents.

In the Examples which follow, all temperatures are in degrees Centigrade unless otherwise stated.

EXAMPLE 1

Preparation of
[1R-[1β-(R*,E,S*),3aα,4β,7aβ]]-6-(octahydro-4-[(1,1-dimethylethyl)-dimethylsilyl]-oxy-7a-methyl-1H-inden-1-yl)-2-methyl-4-heptene-1,2-diol To a cooled (0° C.) suspension of 0.122 g of lithium aluminum hydride and 3.2 ml of dry tetrahydrofuran was added 0.336 g of [1R-[1β-(R*,E,S*),3aα,4β,7aβ]]-6-(octahydro-4-[(1,1-dimethylethyl)dimethylsilyl]oxy-7a-methyl-1H-inden-1-yl)-2-hydroxy-2-methyl-4-heptenecarboxylic-acid methyl ester and 4 ml of dry tetrahydrofuran over 2 minutes. After one hour, 0.061 g of lithium aluminum hydride was added, the mixture stirred for 20 minutes, then the cooling bath was removed. After an additional 2.5 hours, the mixture was recooled at 0° C., 0.6 ml of ethyl acetate was added. After stirring for 10 minutes, 3.5 ml of saturated ammonium chloride solution was added cooling bath removed and the mixture stirred for 25 minutes, and then filtered through Celite washing with chloroform and ethyl acetate. The filtrates were dried over anhydrous sodium sulfate, filtered and concentrated under reduced pressure. The residue was chromatographed on silica gel (hexane-ethyl acetate, 6:4) to give [1R-[1β-(R*,E,S*), 3aα,4β,7aβ]]-6-(octahydro-4-[(1,1-dimethylethyl)dimethylsilyl]-oxy-7a-methyl1H-inden-1-yl)-2-methyl-4-heptene-1,2-diol in 89% yield, $[α]_D^{25}$+48.75° (c O.9388. Chloroform).

EXAMPLE 2

Preparation
[1R-[1β-(R*,E,S*),3aα,4β,7aβ]]-6-(octahydro-4-hydroxy-7a-methyl-1H-inden-1-yl)-2-methyl-4-heptene-1,2-diol To a solution of 0.257 g of [1R-[1β-(R*,E,S*)-,3aα,4β,7aβ,]]-6-(octahydro-4-[1,1-dimethylethyl)-dimethylsilyl]-oxy-7a-methyl-1H-inden-1-yl)-2-methyl-4-heptene-1,2-diol, 3.6 ml of acetonitrile and 3.0 ml of tetrahydrofuran under argon was added 2.8 ml of 48% aqueous hydrogen fluoride. The cloudy mixture was stirred for 3 hours, then poured into 200 ml of chloroform and 20 ml of water. The aqueous phase was extracted 2×100 ml of chloroform and the combined chloroform layers were washed 1×20 ml of saturated sodium bicarbonate. The extract was dried over anhydrous sodium sulfate, filtered and concentrated in vacuo. The residue was chromatographed (ethyl acetate) on silica gel to give 0.176 g (95%) of [1R-[1β-(R*,E,S*), 3aα,4β,7aβ]]-6-(octahydro-4-hydroxy-7a-methyl-1H-inden-1-yl)-2-methyl-4-heptene-1,2-diol, m.p. 87°–88° (methanol-water, 1:1), $[α]_D^{25}$+28.2° (c 0.748, chloroform.

EXAMPLE 3

Preparation of
[1R-[1β-(R*,E,S*),3aα,4β,7aβ]]-octahydro-7a -methyl-4-[2,2,4-trimethyl 1,3-dioxolan-4-yl)-4-butenyl]-1H-inden-4-ol A solution of 0.254 g of [1R-[1β(R*,E,S*),3aα,4β,-7aβ]]-6-(octahydro-4-hydroxy-7a-methyl-1H-inden-1-yl)-2-methyl-4-heptene-1,2-diol, 10 ml of 2,2-dimethoxypropane and 16 mg of p-toluenesulfonic acid monohydrate was stirred under agron at room temperature for 50 minutes, then 2 ml of methanol was added. The mixture was stirred an additional 45 minutes, then 2.5 ml of saturated sodium bicarbonate solution was added. The mixture was stirred for 1 hour, then diluted with 150 ml of chloroform and washed 1×10 ml of water. The aqueous phase was extracted 2×50 ml of chloroform and the combined chloroform layers dried over anhydrous sodium sulfate. The mixture was filtered, concentrated under reduced pressure, and chromatographed on silica gel (hexane-ethyl acetate, 25:75) to give 0.259 (90%) of [1R-[1β-(R*,E,S*),3aα,4β,7aβ]]-octahydro-7a-methyl-1-[1-methyl-4-[(2,2,4-trimethyl 1,3-dioxolan-4-yl)-4-butenyl]-1H-inden-4-ol as an oil; $[α]_D^{25}$+21.27° (c o.6018, chloroform).

EXAMPLE 4

Preparation of [1R-[1β-(R*,S*),3aα,4β,7aβ]-octahydro-7a-methyl-1-[1-methyl-4-(2,2,4-trimethyl-1,3-dioxolan-4-yl)butyl]-1H-inden-4-ol

[1R-[1β-(R*,E,S*),3aα,4β,7aβ]]-Octahydro-7a-methyl-1-[1-methyl-4-[2,2,4-trimethyl-1,3-dioxolan-4-yl)-4- butenyl]-1H-inden-4-ol was hydrogenated at atmospheric pressure over 10% palladium on carbon in ethyl acetate. Filtration and removal of solvent in vacuo gave quantitatively amorphous [1R-[1β-(R*,S*),3aα,4β,-7aβ]]-octahydro-7a-methyl-1-[1-methyl-4-(2,2,4-trimethyl-1,3-dioxolan-4-yl)butyl]-1H-inden-4-ol, $[\alpha]_D^{25}+33.3°$ (c 0.941, chloroform).

EXAMPLE 5

Preparation of [1R-(1R*,S*)-1β,3aα,7aβ]-octahydro-7a-methyl-1-[1-methyl-4-(2,2,4-trimethyl-1,3-dioxolan-4-yl)-butyl]-4H-inden-4-one To a suspension of 1.720 g of 2,2'-bipyridinium chlorochromate and 0.860 g of anhydrous sodium acetate in 10 ml of methylene chloride, was added a solution of 0.500 g of [1R-[1β(R*,S*),3aα,4β,7aβ]]-octahydro-7a-methyl-1-[1-methyl-4-(2,2,4-trimethyl-1,3-dioxolan-4-yl)butyl]-1H-inden-4-ol in 5 ml of methylene chloride and the mixture obtained stirred at room temperature for 2 hours. Additional 0.800 g of 2,2'-bipyridinium chlorochromate was then added and the stirring continued for an additional 2.5 hours. After this time, 1 ml of 2-propanol was introduced and 15 minutes later, the mixture diluted with water and extracted with ether. The combined organic phases were dried, evaporated and the residue purified by fast filtration through silica (eluent: hexane-ethyl acetate, 3:1) to give 0.446 g (90% yield) of pure [1R-(1R*,S*)-1β,3aα,7aβ]]-octahydro-7a-methyl-1-[1-methyl-4-(2,2,4-trimethyl-1,3-dioxolan-4-yl)-butyl]-4H-inden-4-one.

EXAMPLE 6

Preparation of [1R-(1R*,2E,S*),1β,3aα,7aβ]-octahydro-7a-methyl-1-[1-methyl-4-(2,2,4-trimethyl-1,3-dioxolan-4-yl)-2-butenyl]-4H-inden-4-one A solution of 0.145 g of [1R-(1R*,2E,S*),1β,3aα,7aβ]-octahydro-7a-methyl-1-[1-methyl-4-(2,2,4-trimethyl-1,3-dioxolan-4-yl)-2-butenyl]-4H-inden-4-ol in 9 ml of dry methylene chloride was treated with 0.250 g of anhydrous sodium acetate and 0.500 g of 2,2'-bipyridinium chlorochromate and the mixture stirred at room temperature for two hours. After this time, an additional 0.250 g of 2,2'-bipyridinium chlorochromate was added and the stirring continued for two more hours. After this time, 0.5 ml of isopropyl alcohol was added and the mixture stirred for 15 minutes, then diluted with water, and extracted with 3×50 ml of ether. The combined organic phases were washed with water, dried and evaporated to dryness. The residue obtained was purified by chromatography on silica gel, eluting with hexane-ethyl acetate (3:1) to give 0.134 g (93%) of pure [1R-(1R*,2E,S*),1β,3aα,7aβ]-octahydro-7a-methyl-1-[1-methyl-4-(2,2,4-trimethyl-1,3-dioxolan-4-yl)-2-butenyl]-4H-inden-4-one, $[\alpha]_D^{25}$ (c 0.2, ethanol).

EXAMPLE 7

Preparation of 1α,25S,26-trihydroxycholecalciferol 1,3-dimethyl-t-butylsilyl 25,26-acetonide A solution of 1.430 g of [3S-(3α,5β,Z)]-2-[2-methylene-3,5bis-[(1,1-dimethylethyl)dimethylsilyloxy]cyclohexylidene]ethyldiphenylphosphine oxide in 30 ml of anhydrous tetrahydrofuran was treated dropwise and under argon at −78° C. with 1.4 ml of a 1.7 molar solution of n-butyllithium in hexane. Five minutes after the addition was completed, a solution of 0.460 g of [1R-(1R*,S*)-1β,3aα,7aβ]-octahydro-7a-methyl-1-[1-methyl-4-(2,2,4-trimethyl-1,3-dioxolan-4-yl)-butyl]-4H-inden-4-one in 5 ml of anhydrous tetrahydrofuran was added dropwise and the resulting mixture stirred at −78° C. 2.5 hours. It was then treated at −78° C. with 5 ml of a 1N aqueous solution of sodium bicarbonate and potassium-sodium tartrate, allowed to come to room temperature and extracted with ethyl acetate. The combined organic extracts were dried, evaporated and the residue purified by chromatography on silica (using hexane-ethyl acetate 5:1 as eluent) to give 0.91 g (95%) of pure 1α,25S,26-trihydroxycholecalciferol 1,3-dimethyl-t-butylsilyl 25,26-acetonide.

EXAMPLE 8

Preparation of 1α,25S,26-trihydroxycholecalciferol

To a solution of 0.91 g of 1α,25S,26-trihydroxycholecalciferol 1,3-dimethyl-t-butylsilyl 25,26-acetonide in 200 ml of methanol, 46 g of a cation exchange resin (AG 50W-X4, 200–400 mesh from Bio-Rad Laboratory, prewashed with methanol) was added and the mixture stirred at room temperature under argon for 16 hours. After filtration, the methanol solution was evaporated to dryness and the residue redissolved in 100 ml of ethyl acetate and washed 3x with brine. The organic phases were combined, dried, evaporated and the residue purified by chromatography on silica (eluted with ethyl acetate) to give 0.486 g (86% yield) of pure 1α,25S,26-trihydroxycholecalciferol, m.p. 163°-164°, $[\alpha]_D^{25}+58.8°$ (c 0.5, methanol).

EXAMPLE 9

Preparation of 1α,25S,26-trihydroxy-Δ$^{22}$-cholecalciferol

A solution of 0.354 g of [3S-(3α,5β,Z)]-2-[2-methylene-3,5-bis-[(1,1-dimethylethyl)dimethylsilyloxy]-cyclohexylidene]ethyldiphenylphosphine oxide in 8 ml of dry tetrahydrofuran was cooled at −78° C. and treated dropwise under argon with 0.370 ml of a 1.6 molar solution of n-butyllithium in hexane.

After stirring for 5 minutes, a solution of 0.113 g of [1R-(1R*,2E,S*),1β,3aα,7aβ]-octahydro-7a-methyl-1-[1-methyl-4-(2,2,4-trimethyl-1,3-dioxolan-4-yl)-2-butenyl]-4H-inden-4-one in one 2 ml of dry tetrahydrofuran was slowly added and the resulting mixture stirred at −78 C. for two hours. It was then treated with 5 ml of a 1:1 mixture of 1N sodium bicarbonate amd 1N potassium sodium tartrate, allowed to come to room temperature, diluted with water and extracted with 3×75 ml of ethyl acetate. The combined organic extracts were washed with brine, dried and evaporated. The residue was purified by chromatography on silica gel, eluting with hexane-ethyl acetate (9:1) to give 0.220 g of a colorless thick oil. This was dissolved in 25 ml of methanol, treated with 3.5 g of a cation exchange resin [AG 50W-X4, 200-400 mesh, Bio-Rad Laboratories] and stirred overnight. After filtration and washing of the resin with 20 ml of methanol, the solvent was evaporated in vacuo and the residue dissolved in ethyl acetate and washed with 2×30 ml of 2N sodium bicarbonate solution, followed by 3×30 ml of brine. The residue obtained after evaporation of solvent was purified by chromatography on silica gel, eluting with ethyl acetate to give 0.131 g (90%) of pure 1α,25S, 26-trihydroxy-Δ$^{22}$-cholecalciferol as a white, amorphous powder; $[60]_D^{25}+44.9$ (c 0.2, ethanol). EXAMPLE 10

Preparation of
[3S,4S,5S,[3β,4α,5β[(2R*),1R*(1β,3aα,4β,7aβ)]]]-3-[2-(Octahydro-4-hydroxy-7a-methyl-1H-inden-1-yl)propyl]-2,2-dimethyl-4,5-isoxazolidinedicarboxylic acid dimethyl ester A mixture of 7.60 g of [1R[1α(R*,Z),3aβ,4α,7aα]]-octahydro-7a-methyl-1-[1-methyl-3-(methylimino)-propyl]-1H-inden-4-ol N-oxide, 5.70 g of methyl mesaconate, and 4 mL of xylene was heated in a 140° oil bath. The solution, which formed within 5 minutes, was heated for 1 hour and then was cooled to room temperature. Chromatography (silica gel, CH$_2$Cl$_2$/ETOAc, 2:1) afforded 5.42 g (44%) of [3S,4S,5S,[3β,4α,5β[(2R*),1R*(1β,3aα,4β,7aβ)]]]-3-[2-(octahydro-4-hydroxy-7a-methyl-1H-inden-1-yl)-propyl]-2,2-dimethyl-4,5-isoxazolidinedicarboxylic acid dimethyl ester (oil), $[\alpha]_D^{25} = +126.4°$ (c 0.911, CHCl$_3$); m/e 411.

EXAMPLE 11

Preparation of
[3S,4R,5S[3β,4α,5β[(2R*),1R*(1β,3aα,4β,7aβ)]]]-3-[2-(Octahydro-4-hydroxy-7a-methyl-1H-inden-1-yl)propyl]-2,2-dimethyl-4,5-isoxazolidinedimethanol A solution of 10.35 g of [3S,4S,5S[3β,4α,5β[(2R*),1R*(1β,3aα,4β,7aβ)]]]-3-[2-(octahydro-4-hydroxy-7a-methyl-1H-inden-1-yl)propyl]-2,2-dimethyl-4,5-isoxazolidinedicarboxylic acid dimethyl ester, in 30 mL of dry tetrahydrofuran was added dropwise over 30 minutes (argon atmosphere) to a stirred suspension of 4.85 g of lithium aluminum hydride in 150 mL of dry tetrahydrofuran maintaining the temperature between 3° and 8° by means of an ice bath. The suspension was allowed to stir for 1 hour (at 4°) and then 6 mL of water followed by 4 mL of 1N sodium hydroxide were cautiously added. Stirring was continued for about 15 minutes. The suspension was filtered through a glass microfibre filter (Whatman). The filter cake was washed with 6×25 mL of tetrahydrofuran. The combined filtrates, on evaporation of the solvent, afforded 8.32 g of solid residue. The filter cake still contained product and was added to 250 mL of 20% Rochelle salt solution, stirred for 1 hour, and then extracted with 3×150 mL of ethyl acetate. The combined organic phases were dried (sodium sulfate), filtered, and evaporated to give an additional 0.70 g of residue. Thus, the total of [3S,4R,5S[-3β,4α,5β[(2R*),1R*(1β,3aα4β,7aβ)]]]-3-[2-(octahydro-4-hydroxy-7a-methyl-1H-inden-1-yl)propyl]-2,2-dimethyl-4,5-isoxazolidinedimethanol amounted to 9.02 g.

An analytical sample, obtained after liquid chromatography (silica gel, EtOAc/MeOH, 95:5) and recrystallization, had m.p. 151°–152° (EtOAc). $[\alpha]_D^{25} + 108.4°$ (c 0.994, CHCl$_3$), m/e 355.

EXAMPLE 12

Preparation of
[1R-[1α,(3R*,4S*,5R*,6S*),3aβ,4α,7aα]-6-Octahydro-4-hydroxy-7a-methyl-1H-inden-1-yl)-4-(dimethylamino)-3-hydroxymethyl-2-methylheptane-1,2-diol A solution of [3S,4R,5S[3β,4α,5β[(2R*),1R*(1β,3aα,4β,7aβ)]]]-3-[2-(octahydro-4-hydroxy-7a-methyl-1H-inden-1-yl)propyl]-2,2-dimethyl-4,5-isoxazolidinedimethanol from the previous experiment and 2.5 mL of freshly distilled methyl iodide in 10 mL of dry tetrahydrofuran and 50 mL of toluene was heated at 60° (bath) for 3.5 hours and then was evaporated to dryness (aspirator). The methiodide was dissolved in 250 mL of 50% aqueous acetic acid with warming and stirring. After the solution was cooled at room temperature, 9.0 g of zinc dust was added. The suspension was stirred overnight and the residual zinc was removed by filtration and was washed (aq. acetic acid). The pH of the filtrate was adjusted to 11 with 230 mL of concentrated ammonium hydroxide. Extraction with 3×300 mL of CH$_2$Cl$_2$, 2×300 mL of ether, 2×250 mL of 4:1 CH$_2$Cl$_2$/i-PrOH gave 8.7 g of [1R-[1α(3R*,4S*,5R*,6S*),3aβ,4α,7aα]-6-octahydro-4-hydroxy-7a-methyl-1H-inden-1-yl)-4-(dimethylamino)-3-hydroxymethyl-2-methylheptane-1,2-diol. Recrystallization from 350 mL of CH$_2$Cl$_2$ gave 5.90 g of crystals. The mother liquors afforded, after chromatography (silica gel, EtOAc/MeOH/Et$_3$N, 94:1:5), 1.62 g for a total of 7.52 g of the product.

An analytical sample had, m.p. 178°–180° (CH$_2$Cl$_2$). $[\alpha]_D^{25} + 21.7°$ (c 0.986, CHCl$_3$).

EXAMPLE 13

Preparation of
[1R-[1α(1R*,3S*,4R*][4S*],3aβ,4α,7aα]]-Octahydro-7a-methyl-1-[3-(dimethylamino)-4-hydroxy-methyl-1-methyl-4-(2,2,4-trimethyl-1,3-dioxolan-4-yl)-butyl]-1H-inden-4-ol The addition of 3.0 g of p-toluenesulfonic acid monohydrate to a suspension of 4.90 g of [1R-[1α(3R*,4S*,5R*,6S*),3aβ,4α,7aα]]-6-octahydro-4-hydroxy-7a-methyl-1H-inden-1-yl)-4-(dimethylamino)-3-hydroxymethyl-2-methylheptane-1,2-diol in 75 mL of acetone and 4.9 of mL of dimethoxypropane at room temperature produced a clear solution which was stirred (argon atmosphere) for 17 hours. Then, 8 mL of 2N sodium hydroxide was added and the mixture was concentrated with a rotary evaporator (reduced pressure). The residual aqueous suspension was extracted with 4×100 mL of methylene chloride. The combined organic phases were dried (sodium sulfate), filtered, and evaporated to give 5.7 g of product. Purification by medium pressure liquid chromatography (silica gel, hexanes/EtOAc-/Et$_3$N$_3$ 60:30:5) gave 4.79 g of [1R*-[1α-(1R*,3S*,4R*)[4S*],3aβ,4α,7aα]]-octahydro-7a-methyl-1-[3-(dimethylamino)-4-hydroxy-methyl-1-methyl-4-(2,2,4-trimethyl,3-dioxolan-4-yl)-butyl]-1H-inden-4-ol.

An analytical sample had m.p. 104°–105° (pentane/ether, 2:1). $[\alpha]_D^{25} + 19.5°$ (c 0.943, CHCl$_3$).

EXAMPLE 14

Preparation of
[1R-[1α(1R*,E,4R*),[4S*],3aβ,4α,7aα]]-Octahydro-7a-methyl-1-[4-(hydroxymethyl)-1-methyl-4-[(2,2,4-trimethyl-1,3-dioxolan-4-yl)-2-butenyl]-1H-inden-4-ol A solution of [1R-[1α(1R*,3S*,4R*][4S*],3aβ,4α,7aα]]-octahydro-7a-methyl-1-[3-(dimethylamino)-4-hydroxymethyl-1-methyl-4-(2,2,4-trimethyl-1,3-dioxolan-4yl)-butyl]-1H-inden-4-ol and 0.5 mL of freshly distilled methyl iodide in 20 mL of dry toluene and 50 mg of potassium carbonate (anhydrous) was heated at 65° (bath) for 16 hours (argon atmosphere). An additional 0.5 mL of freshly distilled methyl iodide was added and heating continued for 4.5 hours. The reaction mixture was evaporated (reduced pressure) to give the methiodide (2.83 g).

To the above residue was added 10 mL of dry t-butanol and 1.12 g of potassium t-butylate, and the reaction mixture was heated (argon atmosphere) at 55° for 24 hours, then at reflux (100° bath) for 5 hours. The t-butanol was removed on a rotary evaporator. To the residue was added 10 mL of water followed by extraction with 3×50 mL of ether. The combined extracts were dried (sodium sulfate), filtered, and evaporated to give 1.63 g of product. Medium pressure liquid chromatography (silica gel, CH₂Cl₂/EtOAc, 1:1) gave 881 mg of [1R-[1α-(1R*,E,4R*),[4S*],3aβ,4α,7aα]]-octahydro-7a-methyl-1-[4-(hydroxymethyl)-1-methyl-4-[(2,2,4-trimethyl-1,3-dioxolan-4-yl)-2-butenyl]-1H-inden-4-ol.

EXAMPLE 15

Preparation of [1R-[1α(1R*,E,4R*),[4S*],3aβ,4α,7aα]]-Octahydro-7a-methyl-1-[1-methyl-4-[[4-(methylphenyl)sulfonyl]oxy]methyl]-4-[(2,2,4-trimethyl-1,3-dioxolan-4-yl)-2-butenyl]-1H-inden-4-ol To a magnetically stirred solution of 742 mg of [1R-[1α(1R*,E,4R*),[4S*],3aβ,4α,7aα]]-octahydro-7a-methyl-1-[4-(hydroxymethyl)-1-methyl-4-[(2,2,4-trimethyl-1,3dioxolan-4-yl)-2-butenyl]-1H-inden-4-ol and 613 mg of triethylamine in 10 mL of dry methylene chloride, was added at 0° (argon atmosphere) a solution of 385 mg of p-toluenesulfonyl chloride (TsCl) in 4 mL of methylene chloride. After 45 minutes at 0°, the bath was removed. After 5 hours at room temperature an addition of 204 mg of triethylamine and 385 mg of TsCl were added. A third addition was made after 22 hours at room temperature of 204 mg of triethylamine and 385 mg of TsCl. After 7 hours, the reaction was poured into 10 mL of 1N sodium hydroxide. After separation of the phases, the aqueous phase was re-extracted with 2×20 mL of methylene chloride. Each extract was washed in a counter-current manner with 10 mL of 1N sodium hydroxide. The combined organic extracts were dried (sodium sulfate), filtered and evaporated to give 1.35 g of product. Liquid chromatographic separation (silica gel, hexanes/EtOAc, 2:1) gave 840 mg of [1R-[1α(1R*,E,4R*),[4S*],3aβ,4α,7aα]]-octahydro-7a-methyl-1-[1-methyl-4-[[[4-methylphenyl)sulfonyl]oxy]methyl]-4-[(2,2,4-trimethyl-1,3-dioxolan-4-yl)-2-butenyl[-1H-inden-4-ol.

EXAMPLE 16

Preparation of [1R-[1α(1R*,E,4S*),[4S*],3aβ,4α,7aα]]-Octahydro-7a-methyl-1-[1,4-dimethyl-4-[(2,2,4-trimethyl-1,3-dioxolan-4-yl)-2-butenyl]-1H-inden-4-ol To a magnetically stirred suspension of 240 mg of lithium aluminum hydride in 15 mL of dry tetrahydrofuran (argon atmosphere), was added rapidly a solution of 818 mg of [1R-[1α(1R*,E,4R*),[4S*],3aβ,4α,7aα]]-octahydro-7a-methyl-1-[1-methyl-4-[[4-methylphenyl)sulfonyl]oxy]-methyl]-4-[(2,2,4-trimethyl-1,3-dioxolan-4-yl)-2-butenyl]-1H-inden-4-ol. The suspension was heated at reflux for 3 hours, and then was cooled to 0° whereupon 0.4 mL of water followed by 0.6 mL of 1N sodium hydroxide were cautiously added. The resulting mixture was stirred for 15 minutes and then filtered through a glass microfibre filter disc (Whatman). The filter cake was washed with 2×50 mL of tetrahydrofuran. The combined filtrates, on evaporation, gave 641 mg of product. Chromatography (silica gel, hexane/EtOAc, 2:1) afforded 498 mg of [1R-[1α(1R*,E,4S*),[4S*],3aβ,4α,7aα]]-octahydro-7a-methyl-1-[1,4-dimethyl-4-[(2,2,4-trimethyl-1,3-dioxolan-4-yl)-2-butenyl]-1H-inden-4-ol.

An analytical sample had mp 69°–71° (hexanes ). $[\alpha]_D^{25}$ +5.18 (c 1.023, CHCl₃).

EXAMPLE 17

Preparation of [1R-[1β(1R*,2E,4S*),[4S*],3aα,7aβ]]-Octahydro-7a-methyl-1-[1,4-dimethyl-4-[(2,2,4-trimethyl-1,3-dioxolan-4-yl)-2-butenyl]-4H-inden-4-one To a suspension of 1.000 g of 2,2'-bipyridinum chlorochromate and 0.500 g of anhydrous sodium acetate in 10 mL of methylene chloride was added a solution of 0.300 g of [1R-[1β(1R*,2E,4S*),[4S*],3aα,7aβ]]-octahydro-7a-methyl-1-[1,4-dimethyl-4-[(2,2,4-trimethyl-1,3-dioxolan-4-yl)-2-butenyl]-4H-inden-4-ol dissolved in 6 mL of methylene chloride and the mixture obtained stirred at room temperature for 2 hours. Additional 0.500 g of 2,2'-bipyridinum chlorochromate was then added and the stirring continued for an additional 2 hours. After this time, the mixture was treated with 1 mL of 2-propanol and 20 minutes later, diluted with water and extracted with a 1:1 mixture of ether and ethyl acetate. The combined organic phases were washed with water, dried, evaporated and the residue purified by fast filtration through silica (eluent: hexane-ethyl acetate, 4:1) to give 0.284 g of [1R-[1β(1R*,2E,4S*),[4S*],3aα,7aβ]]-octahydro-7a-methyl-1-[1,4-dimethyl-4-[(2,2,4-trimethyl-1,3-dioxolan-4-yl)-2-butenyl]-4H-inden-4-one, $[\alpha]_D^{25}$ = −12.1° (c 0.5 in ethanol).

EXAMPLE 18

Preparation of 1α,25S,26-Trihydroxyergocalciferol

A solution of 665 mg of [3S-(3α,5β,Z)]-2-[2-methylene-3,5-bis[(1,1-dimethylethyl)dimethylsilyloxy]cyclohexylidene]-ethyldiphenyl phosphine oxide in 14 mL of anhydrous tetrahydrofuran was cooled at −78° C. and treated dropwise and under argon with 0.700 mL of a 1.6 molar solution of n-butyllithium in hexane. After stirring for 5 minutes, a solution of 234 mg of [1R-[1β(1R*,2E,4S*),[4S*],3aα,7aβ]]-octahydro-7a-methyl-1-[1,4-dimethyl-4-[(2,2,4-trimethyl-1,3-dioxolan-4-yl)-2-butenyl]-4H-inden-4-one in 3 mL of anhydrous tetrahydrofuran was added dropwise to the deep orange phosphinoxy carbanion solution and the resulting mixture stirred at −78° C. for 1.5 hour. It was then treated with 5 mL of a 1:1 mixture of 2N potassium sodium tartrate and 2N potassium bicarbonate solution, allowed to come to room temperature, diluted with water and extracted with ethyl acetate. The combined organic layers were washed with brine, dried and evaporated to dryness. The residue was purified by fast filtration through silica (eluent: hexane-ethyl acetate, 10:1), then dissolved in a mixture of 1.5 mL of methylene chloride and 12 mL of methanol and stirred at room temperature under argon with 7.5 g of AG 509W-X4-cation exchange resin (200–400 mesh, Bio-Rad Laboratories, Richmond, CA) for 18 hours. After filtration of the resin and washing with methanol, the solvent was evaporated and the residue dissolved in ethyl acetate and washed with 1N potassium bicarbonate solution, then brine, dried and evaporated to dryness. The so obtained material was purified by rapid chromatography on silica, eluting with ethyl acetate to give 248 mg of pure 1α,25S,26-trihydroxycholecalciferol, m.p. 186°–187° C.; $[\alpha]_D^{25}$ +40.2 (c 0.3 in ethanol); ¹H NMR (200 MHz, CD₃OD) 0.53 (s, 3H), 0.98 (d, J=7.2 Hz, 3H) 1.06 (d, J=7.6, 3H), 1.08 (s, 3H), 3.40 (AB q, J$_{AB}$=8.4 Hz, ΔY=16.0 Hz, 2H), 4.14 (m, 1H), 4.34 (m, 1H), 4.90 (s, 1H), 5.26 (dd, J=8.4 Hz, J₂=15.6 Hz, 1H), 5.29 (s, 1H), 5.45 (dd, J₁=7.9 Hz, J₂=15.6 Hz, 1H), 6.08 (d, J=11.6 Hz, 1H), 6.32 (d, J=11.6 Hz, 1H).

EXAMPLE 19

Preparation of
[1R-[1β(R*),3aα,4β,7aβ]]-1-(4-chloro-1-methyl-2-butenyl)-octahydro-4-[[(1,1-dimethylethyl)-dimethylsilyl]oxy]-7a-methyl-1H-indene (2)

A solution of 2.9 g of [1R-[1β,[αS*,βS*],3aα,4aβ,7aβ]]-octahydro-β,7a-dimethyl-4-[[(1,1-dimethylethyl)-dimethylsilyl]oxy]-α-ethenyl-1H-indene-1-ethanol (1) in 100 ml of anhydrous ether was cooled at 0° C. and treated dropwise and under argon with 2.76 ml of thionyl chloride, followed by 0.276 ml of pyridine. The mixture was allowed to stir at 0° C. for 2 hours, then it was quenched by addition of 50 ml of a 2N sodium potassium tartrate solution. The ether phase was separated and the aqueous phase extracted with ethyl acetate. The combined organic phases were washed with 1N hydrochloric acid, water, 2N potassium bicarbonate solution and brine, dried (Na₂SO₄) and evaporated. The solvent evaporated in vacuo and the residue purified by rapid chromatography on silica (eluent: hexane-ethyl acetate, 19:1 (v:v)) to give 2.9 g (95% yield) of pure 2, as a low melting solid.

EXAMPLE 20

Preparation of
[1R-[1β(R*),3aα,4β,7aβ]]-1-[4-(phenylsulfonyl)-1-methyl-2-butenyl)-octahydro-4-[[(1,1-dimethylethyl)-dimethylsilyl]oxy]-7a-methyl-1H-indene(3)

A solution of 2.9 g of the allylic chloride 2 in 130 ml of hexamethylphosphoramide was treated with 10.1 g of benzene sulfinic acid sodium salt and stirred at room temperature under argon for 24 hours. Ice water was then added (130 ml) and, after stirring for 30 minutes, the mixture was extracted with ethyl acetate. The combined extracts were washed with water (6X), dried (Na₂SO₄), evaporated to dryness and the residue purified by rapid chromatography through silica, eluting with hexane-ethyl acetate (39:1 (v:v)) to give 3.5 g (94% yield) of pure 3, as a low melting solid.

EXAMPLE 21

Preparation of
[1R-[1β(R*),3aα,4β,7aβ]]-Octahydro-1-[6,6,6-trifluoro-5-hydroxy-5-(trifluoromethyl)-4-(phenylsulfonyl)-1-methyl-2-hexenyl]-4-[[(1,1-dimethylethyl)-dimethylsilyl]oxy]-7a-methyl-1H-indene (4)

A solution of 0.628 ml of diisopropylamine in 10 ml of anhydrous tetrahydrofuran was cooled at 0° C. and treated dropwise under argon with 2.70 ml (4.32 mmol) of a 1.6 molar solution of n-butyllithium in hexane. After stirring for 15 minutes at 0° C., the resulting solution was cooled at −78° C. and diluted with 17 ml of anhydrous tetrahydrofuran. It was then treated dropwise with a solution of 1.25 g of sulfone 3 in 16 ml of tetrahydrofuran and stirred at −78° C. for 30 minutes. A low stream of hexafluoroacetone was bubbled through the solution, until the yellow color discharged (5 min). After stirring for an additional 5 minutes, the reaction mixture was quenched by addition of 30 ml of a 1:1 mixture of 2N sodium potassium tartrate and 2N potassium bicarbonate solutions, allowed to come to room temperature and extracted with methylene chloride. The combined organic extracts were washed with brine, dried (Na₂SO₄) and evaporated to dryness. The residue was purified by fast chromatography through silica (eluent: hexane-ethyl acetate, 9:1 (v:v)) to give 1.23 g (72% yield) of 4 as a colorless oil.

EXAMPLE 22

Preparation of
[1R]1β(R*)-3aα,4β,7aβ]]-Octahydro-1-[6,6,6-trifluoro-5-hydroxy-5-(trifluoromethyl)-1-methyl-2-hexenyl]-7a-methyl-1H-indene-4-ol (5) and
[1R-[1β(R*),3aα,4β,7aβ]]-Octahydro-1-[6,6,6-trifluoro-5-hydroxy-5-(trifluoromethyl)-1-methyl-3-hexenyl]-7a-methyl-1H-indene-4-ol(6)

A solution of 1.23 g of the sulfone 4 (epimeric mixture) in 40 ml of methanol and 40 ml of tetrahydrofuran was treated with 23 g of dipotassium hydrogen phosphate and after cooling at −20° C., with 24 g of 6% sodium amalgam. After stirring the resulting mixture for 15 minutes, 60 ml of brine was added, allowed to come to room temperature, and then extracted with ethyl acetate. The combined organic extracts were washed with brine, dried (Na₂SO₄) and evaporated to dryness. The residue was purified by chromatography through silica (eluting with hexane-ethyl acetate, 39:1 (v:v)) and the product (0.815 g), dissolved in 40 ml of methanol, was stirred at room temperature with 10 g of AG 50W-X4 cation exchange resin (200–400 mesh, Bio-Rad Laboratories, Richmond, CA) for 6 days. After filtration of the resin and evaporation of the solvent, the residue was purified by 2 consecutive chromatographies on silica, the first one using hexane-ethyl acetate, (9:1 (v:v)) and the second one using methylene chloride to give 200 mg of pure 5 and 50 mg of pure 6.

EXAMPLE 23

Preparation of
[1R-[1β(R*),3aα,4β,7aβ]]-Octahydro-1-[6,6,6-trifluoro-5-hydroxy-5-(trifluoromethyl)-1-methyl-2-hexenyl]-7a-methyl-1H-indene-4-one (7)

A solution of 1182 mg of diol 5 in 2 ml of methylene chloride was added to a slurry of 300 mg of pyridinium chlorochromate in 7 ml of methylene chloride and the resulting mixture stirred at room temperature for 2.5 hours. It was then diluted with 10 ml of ether, stirred for 15 minutes, filtered with Celite ® and the residue triturated several times with ether and the trituration extracts combined and filtered. Evaporation to dryness and purification of the residue by flash chromatography (eluent: hexane-ethyl acetate, 4:1 (v:v)) gave 174 mg (96% yield) of ketone 7.

EXAMPLE 24

Preparation of
[1R-[1β(R*),3aα,4β,7aβ]]-Octahydro-1-[6,6,6-trifluoro-5-(trimethylsilyloxy)-5-(trifluoromethyl)-1-methyl-2-hexenyl]-7a-methyl-1H-inden-4-one (8)

A solution of 174 mg of ketone 7 in 9 ml of methylene chloride was treated with 0.4 ml of trimethylsilylimidazole and stirred at room temperature, under argon for 6 hours. After addition of 1 ml of water, the mixture was stirred for an additional 20 minutes, then diluted with water and extracted with ethyl acetate. The organic extracts were washed with water and brine, dried (Na₂SO₄) and evaporated to dryness. The residue was purified by flash chromatography (eluting with hexane-ethyl acetate, 5:1 (v:v)) to give 177 ml (86% yield) of pure 8.

EXAMPLE 25

Preparation of 26,26,26,27,27,27-Hexafluoro-1α,25-dihydroxy-Δ$^{22}$-cholecalciferol (11)

A solution of 365 mg of [3S-(3α,5β,Z)]-2-[2-methylene-3,5-bis[(1,1-dimethylethyl)dimethylsilyloxy]-cyclohexylidene]ethyldiphenyl phosphine oxide in 10 ml of anhydrous tetrahydrofuran was cooled at −78° C. and treated dropwise and under argon with 0.358 ml of a 1.6 molar solution of n-butyllithium in hexane. After stirring for 5 minutes, a solution of 177 mg of ketone 8 in 2.5 ml of anhydrous tetrahydrofuran was added dropwise to the deep orange phosphinoxy carbanion solution and the resulting mixture stirred at −78° C. for 1 hour. It was then treated with 3 ml of a 1:1 (v:v) mixture of 2N potassium sodium tartrate and 2N potassium bicarbonate solution, allowed to come to room temperature, diluted with water and extracted with ethyl acetate. The combined organic layers were washed with brine, dried and evaporated to dryness. The residue was purified by fast filtration through silica (eluent: hexane-ethyl acetate, 20:1 (v:v)), then dissolved in 0.8 ml of methylene chloride and 9 ml of methanol and stirred at room temperature overnight with 3.5 g of AG 50W-X4 cation exchange resin. After filtration and evaporation of the solvents, the residue was dissolved in 5 ml of tetrahydrofuran and treated with 0.650 ml of a 1 molar solution of tetrabutylammonium fluoride in tetrahydrofuran and stirred for 1 hour. It was then treated with 0.5 ml of water, extracted with ethyl acetate and the combined organic phases washed with water, dried (Na$_2$SO$_4$) and evaporated to dryness. The product was purified by rapid chromatography on silica, eluting with hexane-ethyl acetate (1:2) v:v to give 181 mg (90% yield) of pure product 11, as a white amorphous powder: [α]$^{25}$D+13.9° (c 0.2 in ethanol); $^1$H NMR (400 MHz, CD$_3$OD) 0.69 (s, 3H), 1.03 (d, J=7.2 Hz, 3H), 4.15 (br s, 1H), 4.37 (br s, 1H), 4.90 (s, 1H), 5.29 (s, 1H), 5.45 (m, 2H), 6.09. (d, J=11.2 Hz, 1H), 6.32 (d, J=11.2 Hz, 1H).

EXAMPLE 26

| Injectable Dosage Form Formulation | |
|---|---|
| Ingredient | Amount/ml |
| Sodium Chloride | 1.5 mg |
| Sodium Phosphate, Monobasic | 9.2 mg |
| Disodium Edetate | 1.0 mg |
| Isoascorbic Acid (D) | 10.0 mg |
| Tween 20[(1)] | 4.0 mg |
| 1α,25S,26-(OH)$_3$—Δ$^{22}$-D$_3$ | At desired concentration |
| Sodium Hydroxide | q.s pH 7.0 |
| Water for Injection | q.s. ad |

Method of Preparation (1) Dissolve sodium chloride, sodium phosphate, disodium edetate and isoascorbic acid in water for injection (80% final volume).
(2) In a separate container, dissolve the 1α, 25S,26-(OH)$_3$—Δ$^{22}$-D$_3$ in Tween 20 heated to 60° C. Allow to cool to room temperature (30° C.).
(3) Combine the two solutions and adjust pH to 7.0 with 10% (w/v) sodium hydroxide solution.
(4) Brings to final volume with water for injection.
(5) Aseptically filter and fill this solution.

*Note all processing steps are conducted under nitrogen overlay*
[(1)]Polyoxyalkylene derivative of hexitol anhydride partial long chain fatty acid esters - Sp. pg. 1.08–1.13.

EXAMPLE 27

| Injectable Dosage Form Formulation | |
|---|---|
| Ingredient | Amount/ml |
| Sodium Chloride | 1.5 mg |
| Sodium Phosphate, Monobasic | 9.2 mg |
| Disodium Edetate | 1.0 mg |
| Isoascorbic Acid (D) | 10.0 mg |
| Tween 20 | 4.0 mg |
| 1α,25S,26-(OH)$_3$—D$_2$ | At desired concentration |
| Sodium Hydroxide | q.s pH 7.0 |
| Water for Injection | q.s. ad |

Method of Preparation (1) Dissolve sodium chloride, sodium phosphate, disodium edetate and isoascorbic acid in water for injection (80% final volume).
(2) In a separate container, dissolve the 1α, 25S,26-(OH)$_3$—D$_2$ in Tween 20 heated to 60° C. Allow to cool to room temperature (30° C.).
(3) Combine the two solutions and adjust pH to 7.0 with 10% (w/v) sodium hydroxide solution.
(4) Bring to final volume with water for injection.
(5) Aseptically filter and fill this solution.

*Note all processing steps are conducted under nitrogen overlay*

EXAMPLE 28

| Injectable Dosage Form Formulation | |
|---|---|
| Ingredient | Amount/ml |
| Sodium Chloride | 1.5 mg |
| Sodium Phosphate, Monobasic | 9.2 mg |
| Disodium Edetate | 1.0 mg |
| Isoascorbic Acid (D) | 10.0 mg |
| Tween 20 | 4.0 mg |
| 1α,25R,26-(OH)$_3$—D$_2$ | At desired concentration |
| Sodium Hydroxide | q.s pH 7.0 |
| Water for Injection | q.s. ad |

Method of Preparation (1) Dissolve sodium chloride, sodium phosphate, disodium edetate and isoascorbic acid in water for injection (80% final volume).
(2) In a separate container, dissolve the 1α, 25R,26-(OH)$_3$—D$_2$ in Tween 20 heated to 60° C. Allow to cool to room temperature (30° C.).
(3) Combine the two solutions and adjust pH to 7.0 with 10% (w/v) sodium hydroxide solution.
(4) Bring to final volume with water for injection.
(5) Aseptically filter and fill this solution.

*Note all processing steps are conducted under nitrogen overlay*

EXAMPLE 29

| Oral Dose Form Formulation | |
|---|---|
|  | mg/capsule |
| 1α,25S,26-(OH)$_3$—Δ$^{22}$-D$_2$ | At desired concentration |
| Neobee M5[(1)] | 200.00 |
| Butylated Hydroxyanisole (BHA) | 0.01 |
| Butylated Hydroxytoluene (BHT) | 0.01 |

Method of Preparation (1) Dissolve 1α,25S,26-(OH)$_3$—Δ$^{22}$-D$_2$, BHA and BHT in Neobee M5 under a blanket of nitrogen.
(2) Encapsulate.

[(1)]Medium chain tri-glycerides

EXAMPLE 30

| Oral Dose Form Formulation | |
|---|---|
| | mg/capsule |
| $1\alpha,25S,26\text{-}(OH)_3D_2$ | At desired concentration |
| Neobee M5 | 200.00 |
| Butylated Hydroxyanisole | 0.01 |
| Butylated Hydroxytoluene | 0.01 |

Method of Preparation
(1) Dissolve $1\alpha,25S,26\text{-}(OH)_3\text{—}D_2$, BHA and BHT in Neobee M5 under a blanket of nitrogen.
(2) Encapsulate.

EXAMPLE 31

| Oral Dose Form Formulation | |
|---|---|
| | mg/capsule |
| $1\alpha,25R,26\text{-}(OH)_3\text{—}D_2$ | At desired concentration |
| Neobee M5 | 200.00 |
| Butylated Hydroxyanisole | 0.01 |
| Butylated Hydroxytoluene | 0.01 |

Method of Preparation
(1) Dissolve $1\alpha 25R,26\text{-}(OH)_3\text{—}D_2$, BHA and BHT in Neobee M5 under a blanket of nitrogen.
(2) Encapsulate.

We claim:

1. A method of suppressing immune responses which comprises orally or parenterally administering to a warm-blooded animal requiring such treatment an immunosuppressively effective amount of an ergocalciferol.

2. A method, in accordance with claim 1, wherein the ergocalciferol is 1α-hydroxylated.

3. A method in accordance with claim 2, wherein the ergocalciferol is 1α,25S,26-trihydroxyergocalciferol.

4. A method in accordance with claim 2, wherein the ergocalciferol is 1α,25-dihydroxyergocalciferol.

* * * * *